(12) United States Patent
Pignato et al.

(10) Patent No.: US 12,070,595 B2
(45) Date of Patent: Aug. 27, 2024

(54) DEVICES AND METHODS FOR PERCUTANEOUS ELECTRODE IMPLANT

(71) Applicant: CVRx, Inc., Minneapolis, MN (US)

(72) Inventors: Paul Pignato, Stacy, MN (US); Seth Wilks, Valparaiso, IN (US); Vance Kesler, Roseville, MN (US); James E. Johnson, Winston-Salem, NC (US); James Anderson Smith, Mount Pleasant, SC (US); Peter James Meinz, Minneapolis, MN (US); William Thomas Hartsig, Hudson, WI (US); Caleb Ole Vainikka, Waconia, MN (US)

(73) Assignee: CVRx, Inc., Minneapolis, MN (US)

( * ) Notice: Subject to any disclaimer, the term of this patent is extended or adjusted under 35 U.S.C. 154(b) by 738 days.

(21) Appl. No.: 17/268,192

(22) PCT Filed: Aug. 15, 2019

(86) PCT No.: PCT/US2019/046694
§ 371 (c)(1),
(2) Date: Feb. 12, 2021

(87) PCT Pub. No.: WO2020/037145
PCT Pub. Date: Feb. 20, 2020

(65) Prior Publication Data
US 2021/0316135 A1 Oct. 14, 2021

Related U.S. Application Data

(60) Provisional application No. 62/764,752, filed on Aug. 15, 2018.

(51) Int. Cl.
*A61N 1/05* (2006.01)
*A61N 1/36* (2006.01)

(52) U.S. Cl.
CPC .......... *A61N 1/0502* (2013.01); *A61N 1/056* (2013.01); *A61N 1/36017* (2013.01);
(Continued)

(58) Field of Classification Search
CPC .. A61N 1/0502; A61N 1/056; A61N 1/36017; A61N 1/36117; A61N 1/0551;
(Continued)

(56) References Cited

U.S. PATENT DOCUMENTS 4,863,430 A * 9/1989 Klyce ............... A61M 39/0613
604/170.03
5,665,093 A * 9/1997 Atkins ............... A61B 17/3415
606/1

(Continued)

FOREIGN PATENT DOCUMENTS

| EP | 3263056 A1 | 1/2018 |
|---|---|---|
| WO | WO 2008/134288 A2 | 11/2008 |
| WO | WO 2020/037145 A1 | 2/2020 |

OTHER PUBLICATIONS

Extended European Search Report from EP Application 19850453.2, dated Mar. 16, 2022, 5 pgs.
(Continued)

*Primary Examiner* — David Hamaoui
*Assistant Examiner* — Rumaisa Rashid Baig
(74) *Attorney, Agent, or Firm* — Husch Blackwell LLC

(57) ABSTRACT

Devices and methods of use for introduction and implantation of an electrode as part of a minimally invasive technique. A system includes an introducer tool including a dilator portion, a carrier portion and a release mechanism, the dilator portion selectively engageable with the carrier portion. The system further includes a lead including a lead body and an electrode structure, the electrode structure including an active side with an electrode disposed thereon,
(Continued)

and an inactive side with an element disposed thereon. The introducer tool is configured to be temporarily inserted into a patient over a guidewire, and a portion of the release mechanism is selectively engageable with the element of the electrode structure to retain the electrode structure to the introducer tool.

6 Claims, 19 Drawing Sheets

(52) U.S. Cl.
CPC ........ *A61N 1/36117* (2013.01); *A61N 1/0551* (2013.01); *A61N 2001/0578* (2013.01)

(58) Field of Classification Search
CPC ............ A61N 2001/0578; A61N 1/372; A61B 17/3468; A61M 29/00
See application file for complete search history.

(56) References Cited

U.S. PATENT DOCUMENTS

| | | | |
|---|---|---|---|
| 5,752,939 A * | 5/1998 | Makoto | A61M 1/285 604/523 |
| 6,245,052 B1 * | 6/2001 | Orth | A61M 25/0662 604/93.01 |
| 6,522,926 B1 | 2/2003 | Kieval et al. | |
| 6,605,094 B1 * | 8/2003 | Mann | A61B 17/3401 606/129 |
| 6,850,801 B2 | 2/2005 | Kieval et al. | |
| 6,985,774 B2 | 1/2006 | Kieval et al. | |
| 7,480,532 B2 | 1/2009 | Kieval et al. | |
| 7,499,747 B2 | 3/2009 | Kieval et al. | |
| 7,655,014 B2 * | 2/2010 | Ko | A61M 25/0668 606/129 |
| 7,835,797 B2 | 11/2010 | Rossing et al. | |
| 7,840,271 B2 | 11/2010 | Kieval et al. | |
| 8,086,314 B1 | 12/2011 | Kieval | |
| 8,326,430 B2 | 12/2012 | Gerogakopoulos et al. | |
| 8,437,867 B2 * | 5/2013 | Murney | A61N 1/3616 607/116 |
| 8,718,793 B2 * | 5/2014 | O'Connor | A61N 1/0587 607/119 |
| 9,345,877 B2 * | 5/2016 | Pignato | A61N 1/3752 |
| 2003/0045892 A1 * | 3/2003 | Kaladelfos | A61B 17/0469 606/148 |
| 2004/0186529 A1 | 9/2004 | Bardy et al. | |
| 2006/0004417 A1 * | 1/2006 | Rossing | A61N 1/36114 607/9 |
| 2006/0004421 A1 | 1/2006 | Bennett et al. | |
| 2006/0074453 A1 | 4/2006 | Kieval et al. | |
| 2006/0111753 A1 * | 5/2006 | Imran | A61N 1/0509 607/40 |
| 2008/0082137 A1 | 4/2008 | Kieval et al. | |
| 2008/0103407 A1 | 5/2008 | Bolea et al. | |
| 2008/0269740 A1 * | 10/2008 | Bonde | A61N 1/0551 606/53 |
| 2008/0312578 A1 * | 12/2008 | DeFonzo | A61M 25/0032 604/6.16 |
| 2009/0192579 A1 * | 7/2009 | Ransbury | A61M 39/0613 607/119 |
| 2010/0318098 A1 * | 12/2010 | Lund | A61N 1/0524 606/129 |
| 2011/0054485 A1 | 3/2011 | Kullas et al. | |
| 2011/0152763 A1 * | 6/2011 | Bishop | A61M 29/00 604/101.01 |
| 2011/0152914 A1 * | 6/2011 | Ostrovsky | A61F 2/0045 606/193 |
| 2011/0172767 A1 * | 7/2011 | Rathi | A61B 17/0401 156/60 |
| 2011/0190792 A1 * | 8/2011 | Chu | A61B 17/06109 606/144 |
| 2012/0071896 A1 * | 3/2012 | Ferree | A61B 17/06061 606/139 |
| 2012/0109250 A1 * | 5/2012 | Cates | A61N 1/36117 607/44 |
| 2012/0310323 A1 * | 12/2012 | Roeder | A61F 2/966 623/1.12 |
| 2014/0107709 A1 | 4/2014 | Schmitz et al. | |
| 2015/0133952 A1 * | 5/2015 | Seifert | A61B 17/3415 607/116 |
| 2015/0201848 A1 * | 7/2015 | Stalker | A61M 25/0074 600/486 |
| 2015/0251002 A1 * | 9/2015 | Williams | A61B 5/6821 607/54 |
| 2015/0343228 A1 * | 12/2015 | Strommer | A61N 1/3956 606/129 |
| 2017/0007826 A1 | 1/2017 | Cates et al. | |
| 2017/0027688 A1 * | 2/2017 | Backus | A61F 2/243 |
| 2017/0258516 A1 * | 9/2017 | Sato | A61B 17/1227 |
| 2017/0325952 A1 * | 11/2017 | Whelton | A61F 2/2439 |
| 2018/0071517 A1 * | 3/2018 | Fruci | A61B 46/17 |
| 2019/0030280 A1 * | 1/2019 | Yokoyama | A61M 25/0054 |

OTHER PUBLICATIONS

International Search Report and Written Opinion for PCT Application PCT/US2019/046694 dated Nov. 19, 2019, 19 pgs.
Boston Scientific, "User's Manual EMBLEM™ S-ICD Electrode Delivery System Model 4712", 2017, 44 pgs, http://www.bostonscientific.com/content/dam/Manuals/us/current-rev-en/360244-001_EMBLEM_UM_en-USA_S.pdf, accessed Mar. 1, 2021.
Boston Scientific, "User's Manual EMBLEM™ S-ICD Subcutaneous Electrode Insertion Tool Model 4711", 2017, 28 pgs, http://www.bostonscientific.com/content/dam/Manuals/us/current-rev-en/359471-003_EMBLEM_UM_en-USA_S.pdf, accessed Mar. 1, 2021.
International Preliminary Report on Patentability from PCT Application PCT/US2019/046694, dated Feb. 25, 2021, 6 pgs.

* cited by examiner

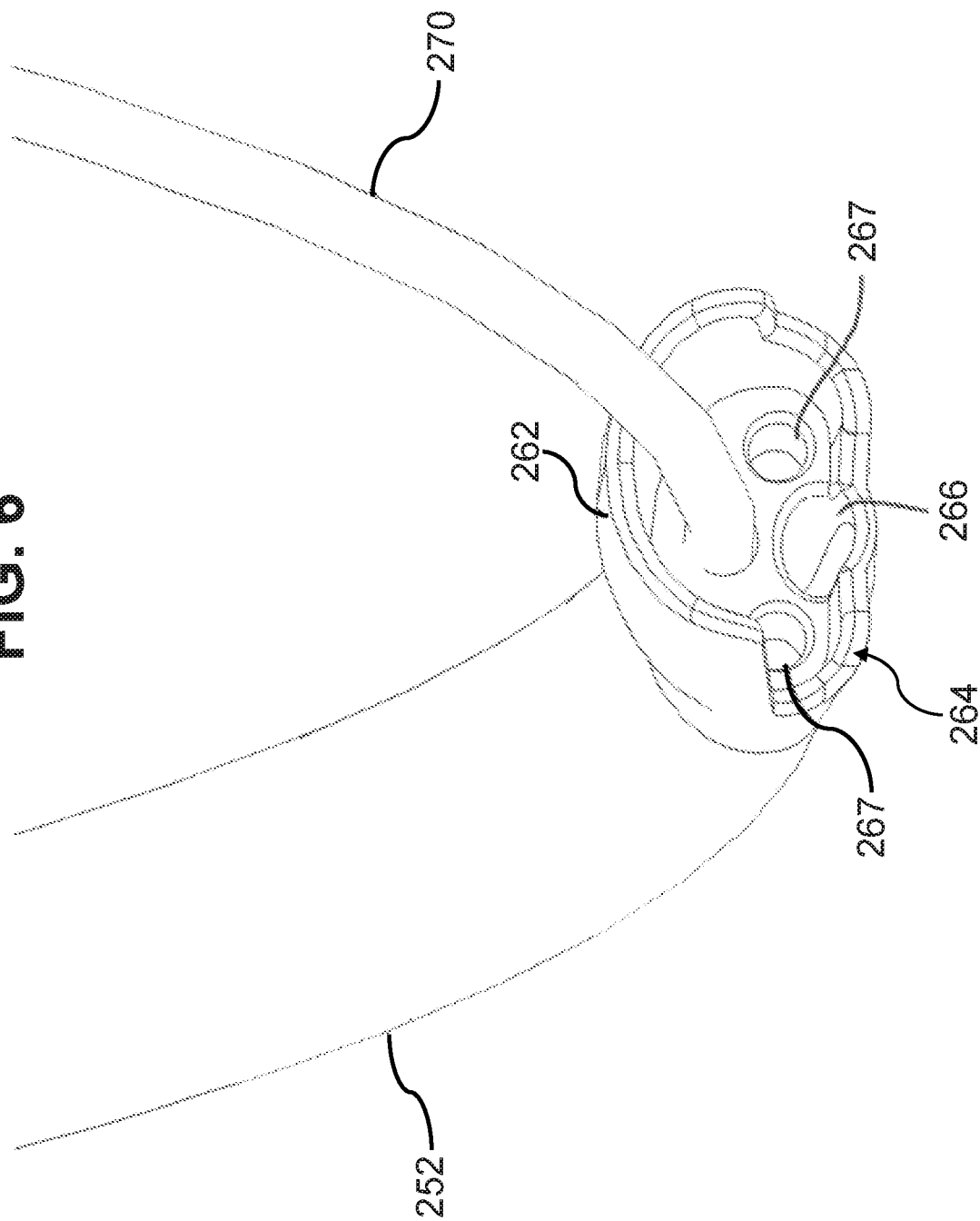

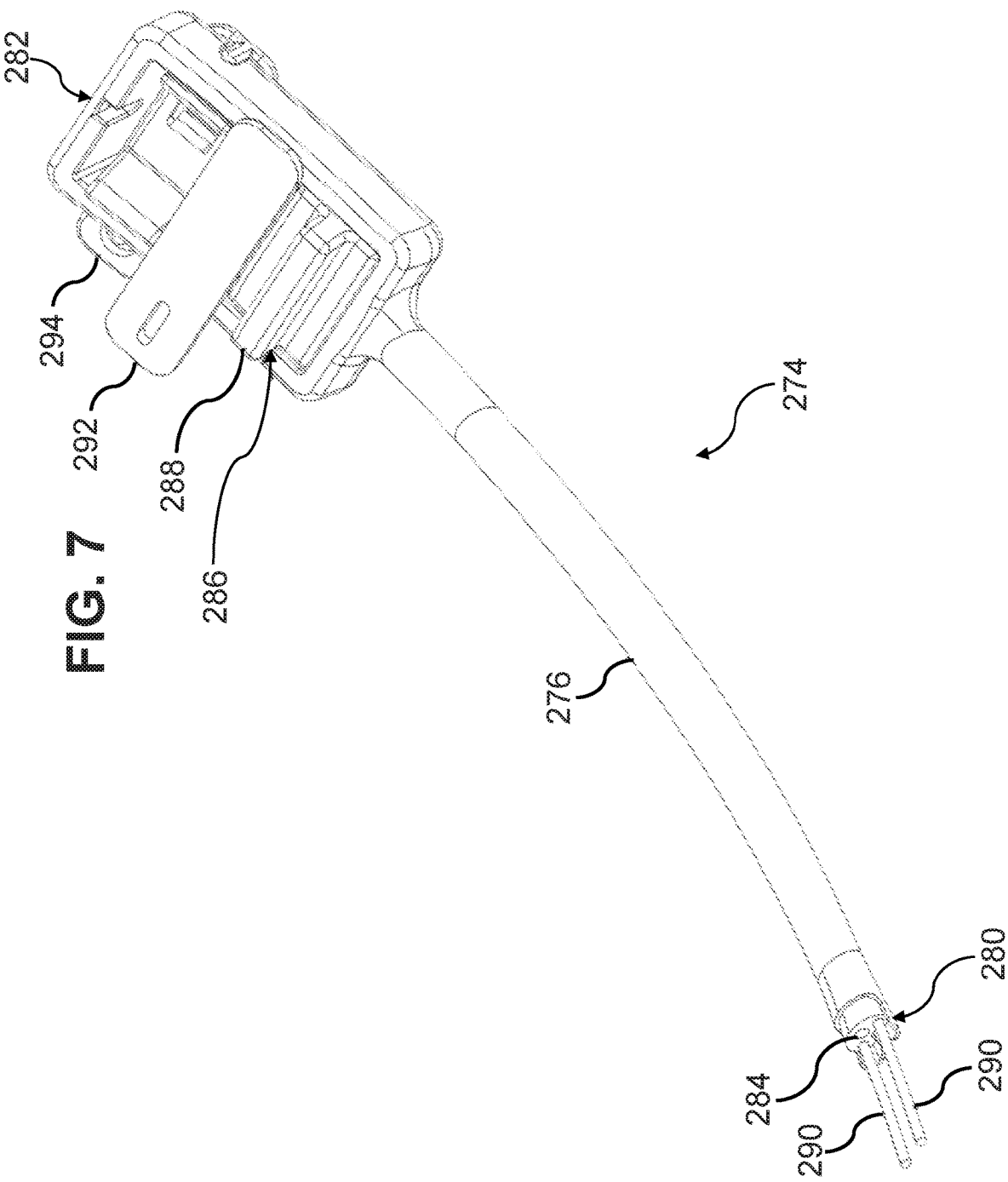

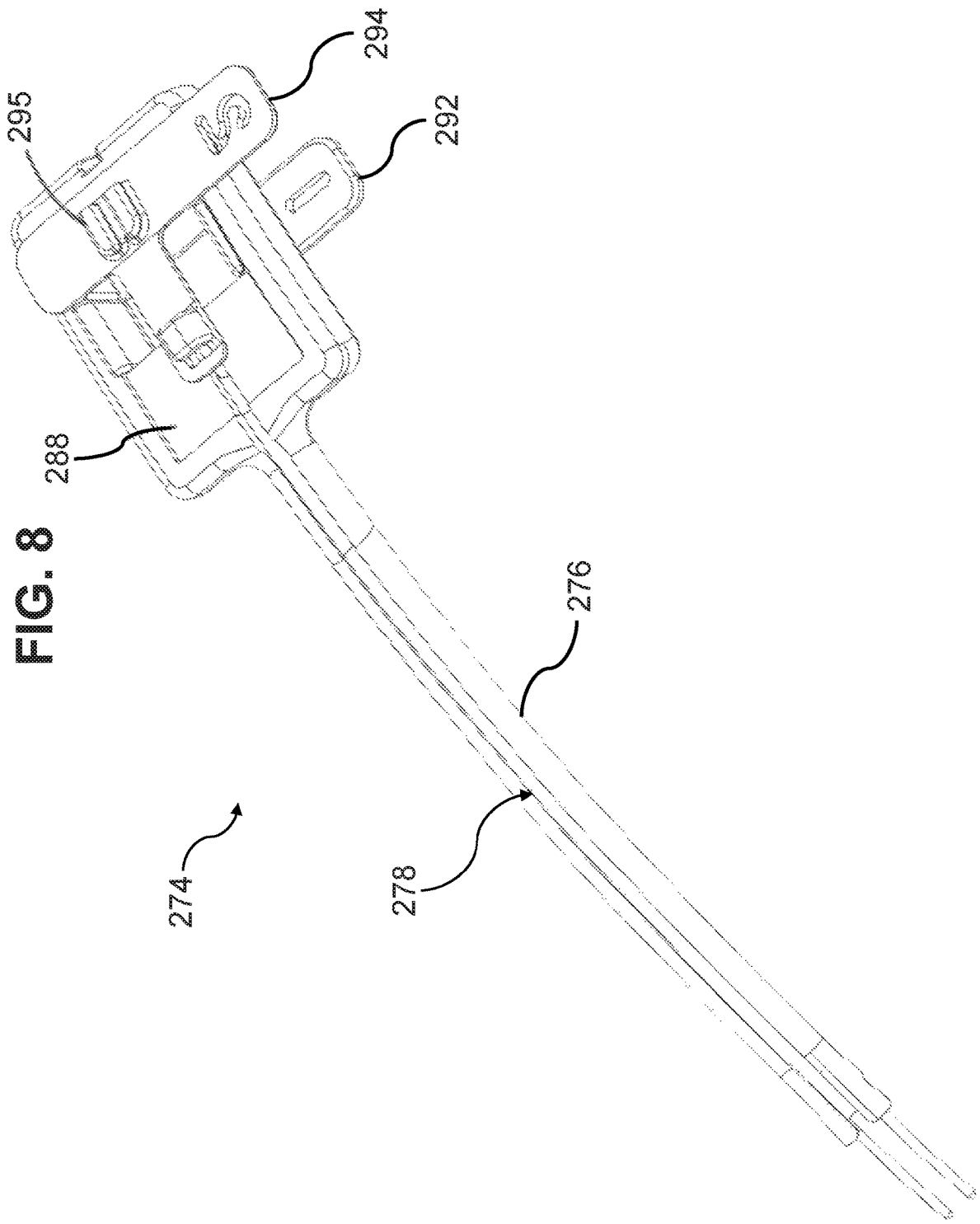

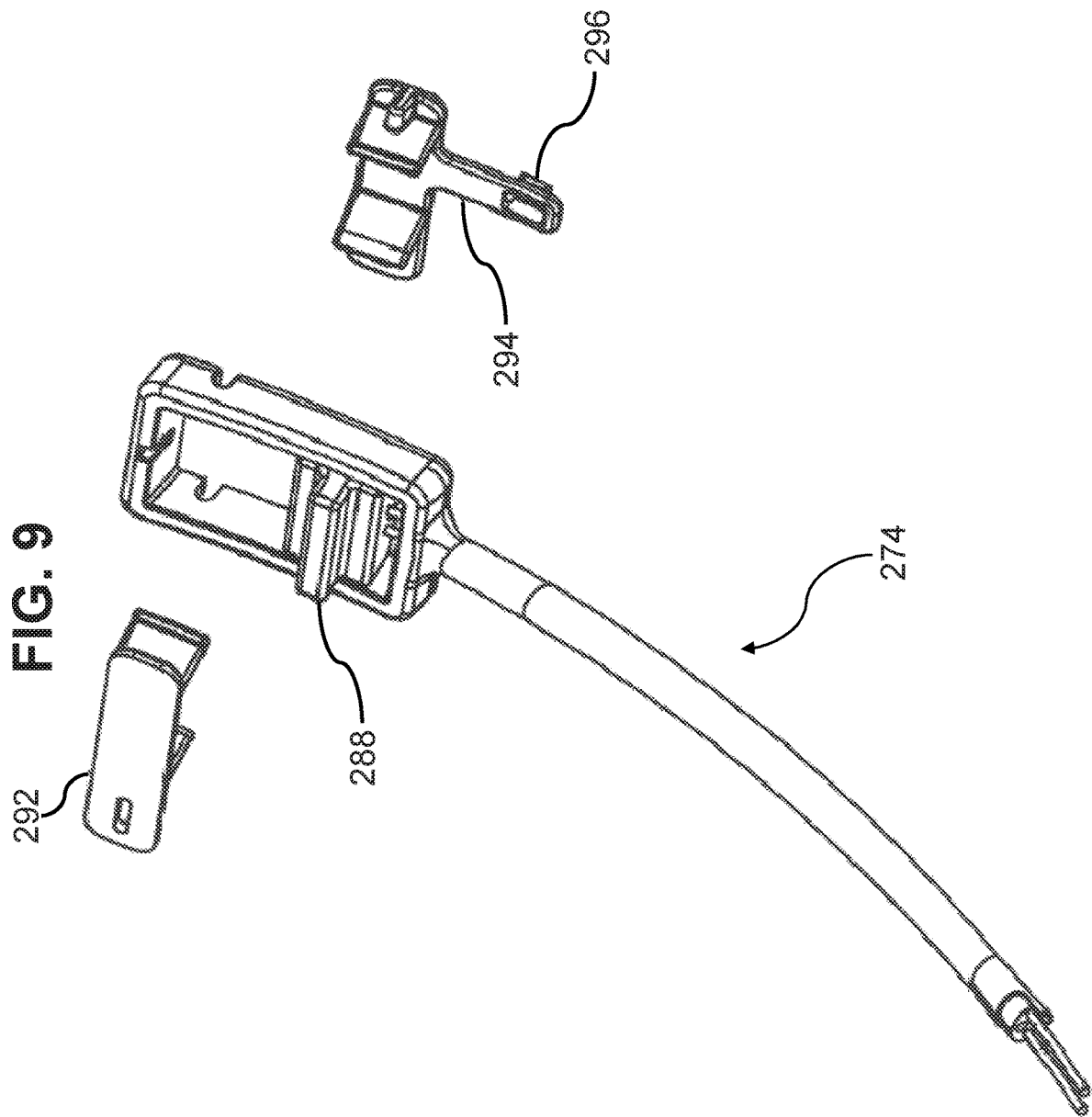

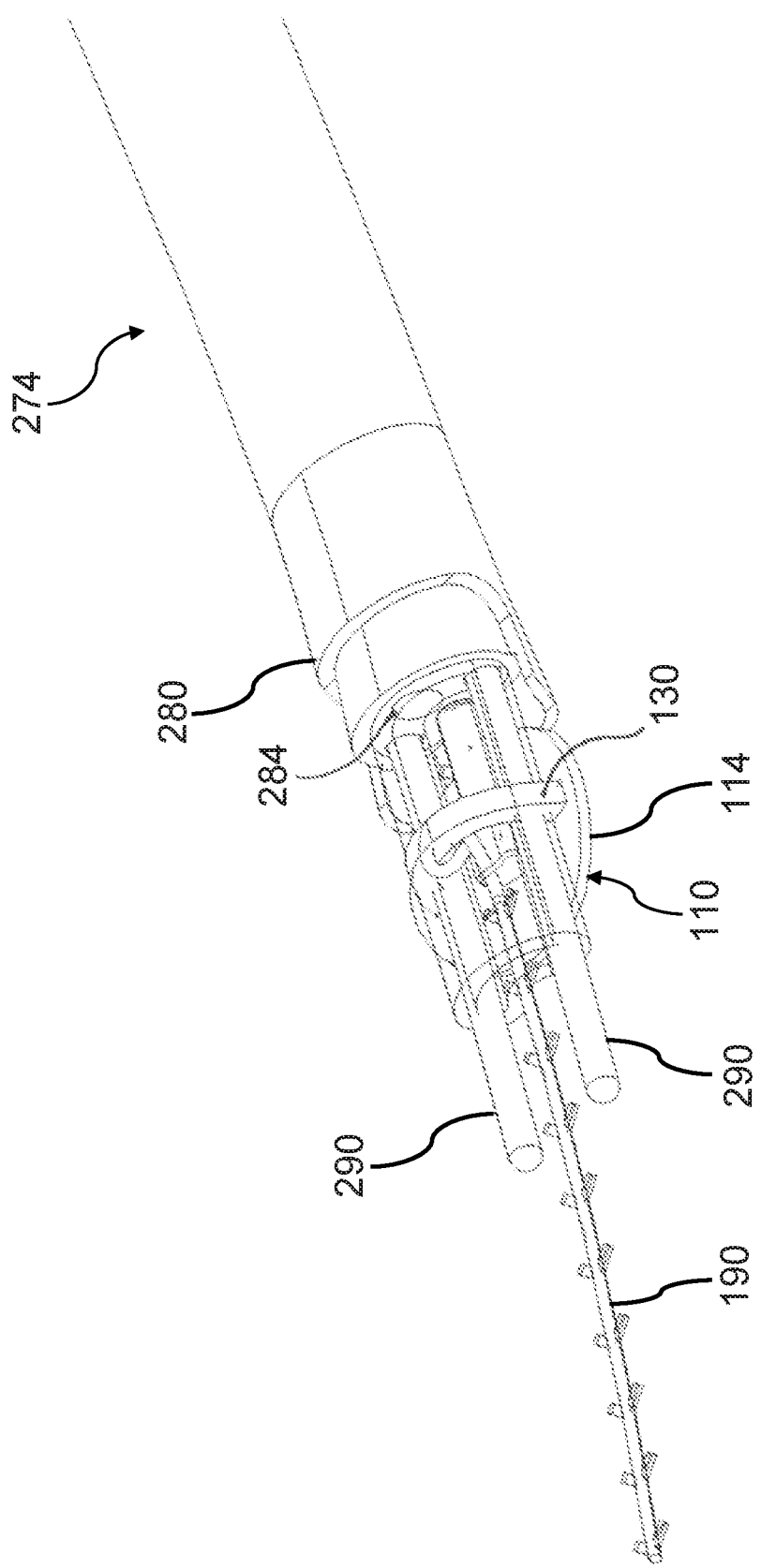

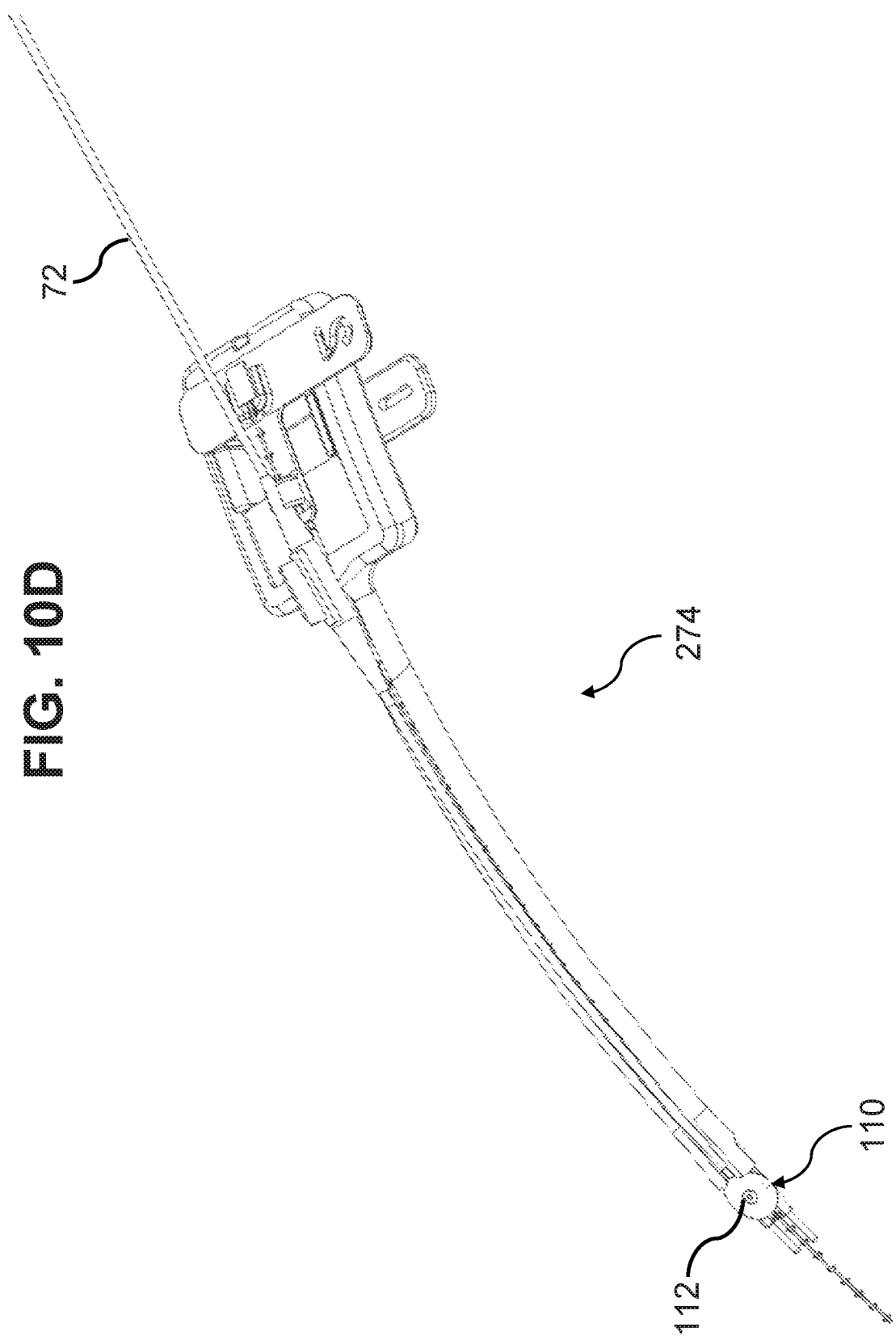

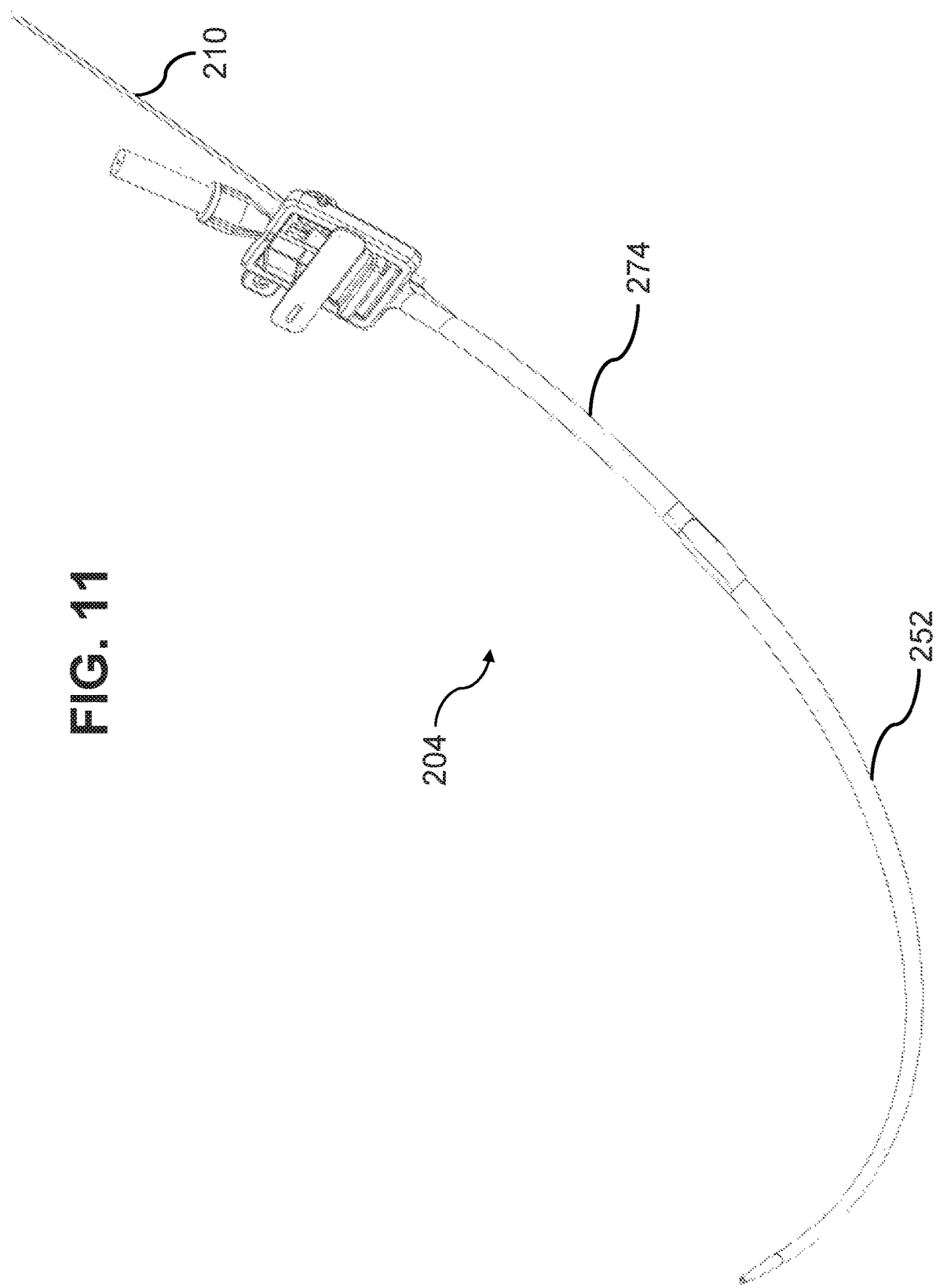

DEVICES AND METHODS FOR PERCUTANEOUS ELECTRODE IMPLANT

CROSS-REFERENCE TO RELATED APPLICATIONS

This application is a National Stage entry of PCT/US2019/046694, filed Aug. 15, 2019, which claims priority to U.S. Provisional Application 62/764,752, filed Aug. 15, 2018, the disclosures of which are hereby incorporated by reference in their entireties.

TECHNICAL FIELD

The present disclosure relates generally to surgical implant methods and devices, and more particularly the present disclosure relates to improved minimally invasive methods and devices for implanting one or more components of a baroreflex activation device.

BACKGROUND

Cardiovascular disease is a major contributor to patient illness and mortality, and is also a primary driver of health care expenditure. Heart failure is the final common expression of a variety of cardiovascular disorders, characterized by an inability of the heart to pump enough blood to meet a patient's needs. Symptoms of heart failure include fatigue, reduced exercise capacity and poor survival.

Hypertension, or high blood pressure, is a major cardiovascular disorder that is estimated to affect tens of millions of people in the United States alone. Hypertension is a leading cause of heart failure and stroke, is the primary cause of death for tens of thousands of patients per year, and is listed as a primary or contributing cause of death for hundreds of thousands of patients per year in the United States alone.

Accordingly, heart failure and hypertension are serious health problems demanding significant research and development for the treatment thereof.

One method of treating hypertension and/or heart failure is baroreflex activation therapy (or "BAT"), which comprises stimulation of baroreceptors and/or associated nerves or nerve structures. Baroreceptors are sensory nerve ends that are profusely distributed within the walls of the major arteries, as well in the heart, aortic arch, carotid sinus or arteries, and in the low-pressure side of the vasculature such as the pulmonary artery and vena cava. Baroreceptor signals are used to activate a number of body systems which collectively may be referred to as the baroreflex system. Baroreceptors are connected to the brain via the nervous system. Thus, the brain is able to detect changes in blood pressure, which can be related to, or indicative of, cardiac output.

Baroreflex activation therapy works by artificially activating the carotid sinus baroreflex. U.S. Pat. No. 6,522,926 to Kieval, et al. discloses a baroreflex activation system and method for activating baroreceptors to regulate blood pressure for the treatment of hypertension and/or heart failure (to counteract the above-described pressor response). Generally speaking, the baroreceptor activation device may be activated, deactivated or otherwise modulated to activate one or more baroreceptors and induce a baroreceptor signal or a change in the baroreceptor signal to thereby affect a change in the baroreflex system. The baroreceptor activation device may be activated, deactivated, or otherwise modulated continuously, periodically, or episodically. The baroreceptor activation device may utilize electrical, mechanical, thermal, chemical, or biological means, or a combination thereof to activate the baroreceptor. The baroreceptor may be activated directly, or activated indirectly via the adjacent vascular tissue.

Activating the baroreflex (by, for example, stimulation of baroreceptors in the aortic arch or carotid sinus or by stimulating the nerve emanating from baroreceptors such as the aortic nerve, carotid sinus nerve or vagus nerve) increases afferent electrical signals. For example, through the carotid sinus nerve (Hering's nerve, a branch of the glossopharyngeal nerve, cranial nerve IX) or aortic nerve (a branch of the vagus nerve, cranial nerve X) to the medullary brain centers that regulate autonomic tone. Increased afferent signals to these medullary centers cause a reduction in sympathetic tone and an increase in parasympathetic tone. This results in lower heart rate, reduced sodium and water reabsorption by the kidney resulting in a diuresis, relaxation of the smooth muscle in the blood vessels which results in vasodilatation and a reduction in excessive blood pressure, cardiac workload and circulating neurohormone levels.

Thus, peripheral activation of the baroreflex results in a physiologic response whereby cardiovascular function is controlled by mechanisms determined by the integrative action of the central nervous system action on all peripheral organs and blood vessels. In hypertension clinical trials, BAT has been demonstrated to reduce excessive blood pressure. In heart failure clinical trials, BAT has been demonstrated to reduce patient symptoms, improve patient quality of life and functional capacity, improve cardiac function, decrease levels of circulating cardiac stress biomarkers, and reduce patient rehospitalization.

Early approaches to implanting BAT systems typically required relatively large incisions on one or both sides of a patient's neck to create sufficient access to the vasculature. The carotid artery was dissected free, one or more electrode pads were wrapped around the artery and sutured in place. These procedures were performed by surgeons, with the patient placed under general anesthesia, and although similar to a routine procedure performed by vascular surgeons, carried a risk profile typically associated with surgical procedures. As expected, such procedures required the use of expensive operating facilities, staff, and equipment.

Current generation implantable baroreflex therapy systems offer pulse generators and electrodes with reduced form factors as compared to early systems. One such system, described in U.S. Pat. No. 8,437,867 to Murney et al., includes an implantable pulse generator and associated circuitry contained within a hermetically sealed housing, an elongate flexible electrical lead connectable to the housing, and a monopolar electrode structure coupled with the electrical lead.

Current generation BAT systems offer improvements to the implant procedure. Smaller electrode structures typically allow smaller incisions on the patient. The electrode structure described in the above-mentioned U.S. Pat. No. 8,437,867 can be implanted via a minimally invasive approach, as described therein. However, the opportunity exists for further improvements to the speed, simplicity and invasiveness of the implant procedure.

SUMMARY

The following are some objectives of the present disclosure:
Enable a baroreflex therapy system to be implanted by electrophysiologists (EPs) and interventional cardiologists in a standard cathlab or hybrid cathlab
Eliminate the need for a full cut-down to the carotid sinus
Eliminate the need for administering general anesthesia to the patient
Eliminate the need to fixate the electrode onto the carotid artery with sutures
Enable ultrasound guided electrode/lead delivery to extravascular surface of carotid sinus via a small (approximately one inch or less) incision in the neck.

In an embodiment, a system comprising an introducer tool including a dilator portion, a carrier portion and a release mechanism, the dilator portion selectively engageable with the carrier portion. The system further includes a lead including a lead body and an electrode structure, the electrode structure including an active side with an electrode disposed thereon, and an inactive side with an element disposed thereon. The introducer tool is configured to be temporarily inserted into a patient over a guidewire, and a portion of the release mechanism is selectively engageable with the element of the electrode structure to retain the electrode structure to the introducer tool.

In an embodiment, a device comprises a dilator portion including a dilator body, a hypotube coupled to and extending from the dilator body, and a port disposed in the dilator body. The device further includes a carrier portion including a carrier body and a carrier lumen disposed therein, and still further includes a release mechanism coupled to the carrier portion, the release mechanism including a movable pin and an actuator, the actuator operable to selectively advance and retract the pin with respect to the carrier body. The dilator portion and the carrier portion are selectively engagable, the hypotube of the dilator portion insertable into the carrier lumen, and further wherein the pin in an advanced position extends into the port of the dilator portion.

In an embodiment, a method comprises providing a system to a user, the system including an introducer tool including a dilator portion, a carrier portion and a release mechanism, the dilator portion selectively engageable with the carrier portion, wherein the release mechanism includes a movable pin and an actuator, the actuator operable to selectively advance and retract the pin with respect to the carrier body. The system further includes a lead including a lead body and an electrode structure, the electrode structure including an active side with an electrode disposed thereon, and an inactive side with an element disposed thereon. The method further comprises providing instructions recorded on a tangible medium to the user, the instructions for implanting the lead in a patient including inserting the introducer tool through a skin of the patient, positioning the introducer tool such that the electrode structure is proximate an intended implant location, manipulating the release mechanism to disengage the dilator portion from the carrier portion, removing the dilator portion from the patient, further manipulating the release mechanism to disengage the movable pin from the element of the electrode structure so as to release the electrode structure from the carrier portion, and removing the carrier portion from the patient.

BRIEF DESCRIPTION OF THE DRAWINGS

Subject matter hereof may be more completely understood in consideration of the following detailed description of various embodiments in connection with the accompanying figures, in which:

FIG. 6 is a closeup view of a second end of the dilator portion of FIG. 5.

FIG. 7 is a perspective view of the electrode carrier portion of the system of FIG. 2.

FIG. 8 is another perspective view of the electrode carrier portion of FIG. 7, from the opposite side.

FIG. 9 is an exploded view of the electrode carrier portion of FIG. 7.

FIG. 10C is a closeup view of a first end of the electrode carrier portion of FIG. 10A.

FIG. 10D is another perspective view of the electrode carrier portion, electrode structure, and lead of FIG. 10B, from the opposite side.

FIG. 11 is a perspective view of a lead delivery tool of the system of FIG. 2.

Figure 1:
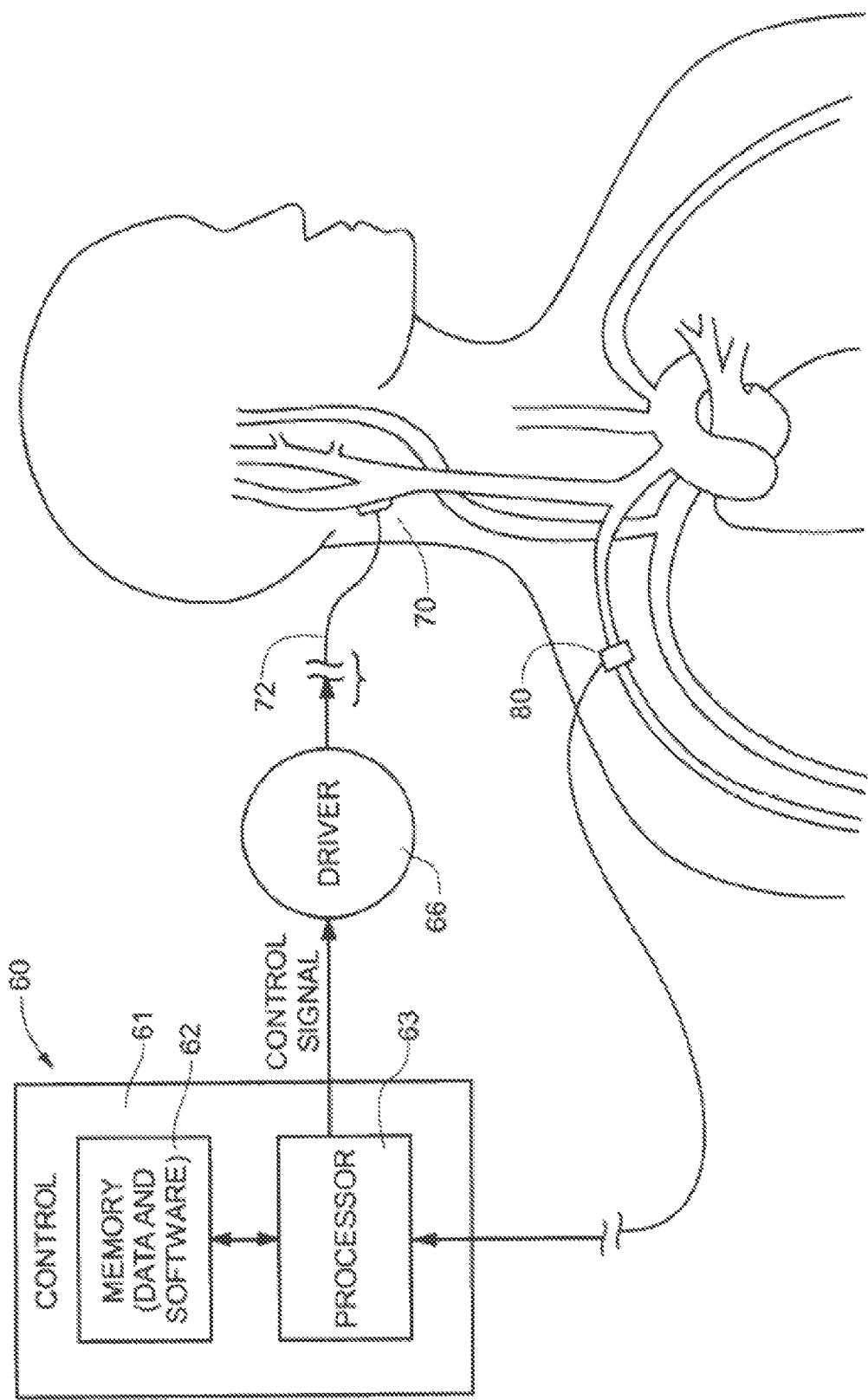
FIG. 1 is a schematic illustration of a baroreflex activation system, according to embodiments of the present disclosure.

While various embodiments are amenable to various modifications and alternative forms, specifics thereof have been shown by way of example in the drawings and will be described in detail. It should be understood, however, that the intention is not to limit the 5 disclosure to the particular embodiments described. On the contrary, the intention is to cover all modifications, equivalents, and alternatives falling within the spirit and scope of the subject matter as defined by the claims.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

Embodiments of the present disclosure generally pertain to improved devices and methods for implanting a baroreflex activation therapy system. In an embodiment, the baroreflex activation therapy system can be as described in U.S. Pat. No. 8,437,867 to Murney et al., the disclosure of which is incorporated by reference herein.

For information pertaining to the cardiovascular, circulatory and nervous systems, as well as baroreceptor and baroreflex therapy systems that may be used in whole or in part with embodiments of the present disclosure, reference is made to the following commonly assigned published applications and patents: U.S. Published Patent Application Nos.

2006/0004417 to Rossing et al., 2006/0074453 to Kieval et al., 2008/0082137 to Kieval et al., and U.S. Pat. No. 6,522,926 to Kieval et al., U.S. Pat. No. 6,850,801 to Kieval et al., U.S. Pat. No. 6,985,774 to Kieval et al., U.S. Pat. No. 7,480,532 to Kieval et al., U.S. Pat. No. 7,499,747 to Kieval et al., U.S. Pat. No. 7,835,797 to Rossing et al., U.S. Pat. No. 7,840,271 to Kieval et al., U.S. Pat. No. 8,086,314 to Kieval, U.S. Pat. No. 8,326,430 to Georgakopoulos et al., and U.S. Pat. No. 9,345,877 to Pignato et al., the disclosures of which are hereby incorporated by reference in their entireties except for the claims and any expressly contradictory definitions.

Referring now to FIG. 1, an embodiment of a baroreflex activation therapy system is depicted, including a control system 60, a baroreflex activation device 70, and optionally one or more sensor(s) 80. The control system 60 may include a therapy block 61 comprising a processor 63 and a memory 62. Control system 60 is configured to be implanted within a patient and is enclosed within a housing, or can, and is communicably coupled to baroreflex activation device 70 such as by way of lead 72, or by wireless means such as radiofrequency or other forms of wireless communication. Lead 72 may include an optional attachment tab 73, which may be used to suture or otherwise attach lead 72 to a patient in order to provide strain relief to the electrode-tissue interface. Control system 60 includes a driver 66 to provide the desired power mode for the baroreceptor activation device 70. For example if the baroreceptor activation device 70 utilizes electrical actuation, the driver 66 may comprise a power amplifier, pulse generator or the like to selectively deliver electrical control signals via lead 72. As used herein, the words "housing," "enclosure," "case" and "can" are synonymous when used to refer to the housing of the implantable pulse generator. At least a portion of the housing is conductive for use as an electrode in conjunction with the monopolar electrode structure on the lead. Such a housing may be referred to as an active can.

In an embodiment, baroreceptor activation device 70 comprises an electrode structure 110. In an embodiment, electrode structure 110 is considered to be part of lead 72. Electrode structure 110 generally includes an electrode 112 mounted on, integrated with, or otherwise coupled to a backer 114. Electrode 112 may comprise platinum iridium, and may include a surface treatment, such as iridium oxide or titanium nitride and/or can include steroid, anti-inflammatory, antibiotic and/or analgesic compounds, for example. Backer 114 may be constructed of Dacron-reinforced insulated silicone, or other suitable materials that are flexible, sturdy, electrically insulative and/or suitable for implantation in a body. Backer 114 and/or electrode 112 may comprise circular structures, or other suitable arrangements without departing from the spirit of the invention. For example backer 114 may include one or more tabs or features configured for facilitating fixation to tissue. In one embodiment, electrode 112 may have a diameter of about 1 mm, and backer 114 may have a diameter of about 6 mm. However, it is contemplated that electrode 112 may have a diameter within a range of about 0.25 mm-3 mm, while backer 114 may have a diameter within a range of about 1 mm-10 mm. In one embodiment the diameter of backer 114 is at least twice the diameter of electrode 112.

Electrode 112 comprises a cathode, and in one embodiment the housing of control system 60 may comprise an anode. In another embodiment, an anode may be provided as part of lead 72. In another embodiment, an anode is provided on a second lead which is also coupled to control system 60. In all embodiments the anode is preferably sufficiently larger than the cathode, for example ten times larger. In another embodiment the anode is fifty times larger than the cathode. Further, the anode and cathode are preferably positioned at a minimum distance away from one another, for example, the distance may be about twenty times the cathode diameter. In another embodiment, the distance between anode and cathode is at least fifty times the cathode diameter.

One or more electrode structures 110 may be provided as part of a baroreflex activation therapy system according to embodiments. For example, a first electrode structure 110 may be positioned at a first anatomical location, while a second electrode structure 110 is positioned at a second anatomical location, such as for example at a left carotid sinus and a right carotid sinus. Or a first electrode structure 110 may be positioned at a first anatomical location while a second electrode structure is positioned at a second anatomical location proximate the first anatomical location, such as for example positioning first and second electrode structures proximate one another on the left carotid sinus and/or carotid arteries.

Figure 10A:
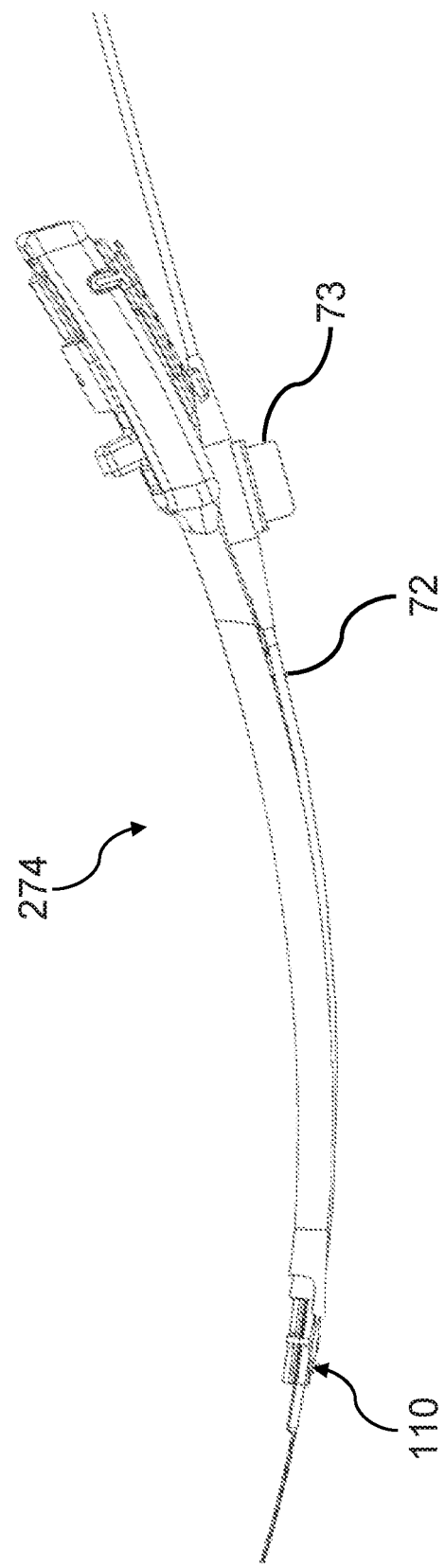
FIG. 10A is a side view of the electrode carrier portion of the system of FIG. 2, coupled to an electrode structure and a lead.
Figure 10B:
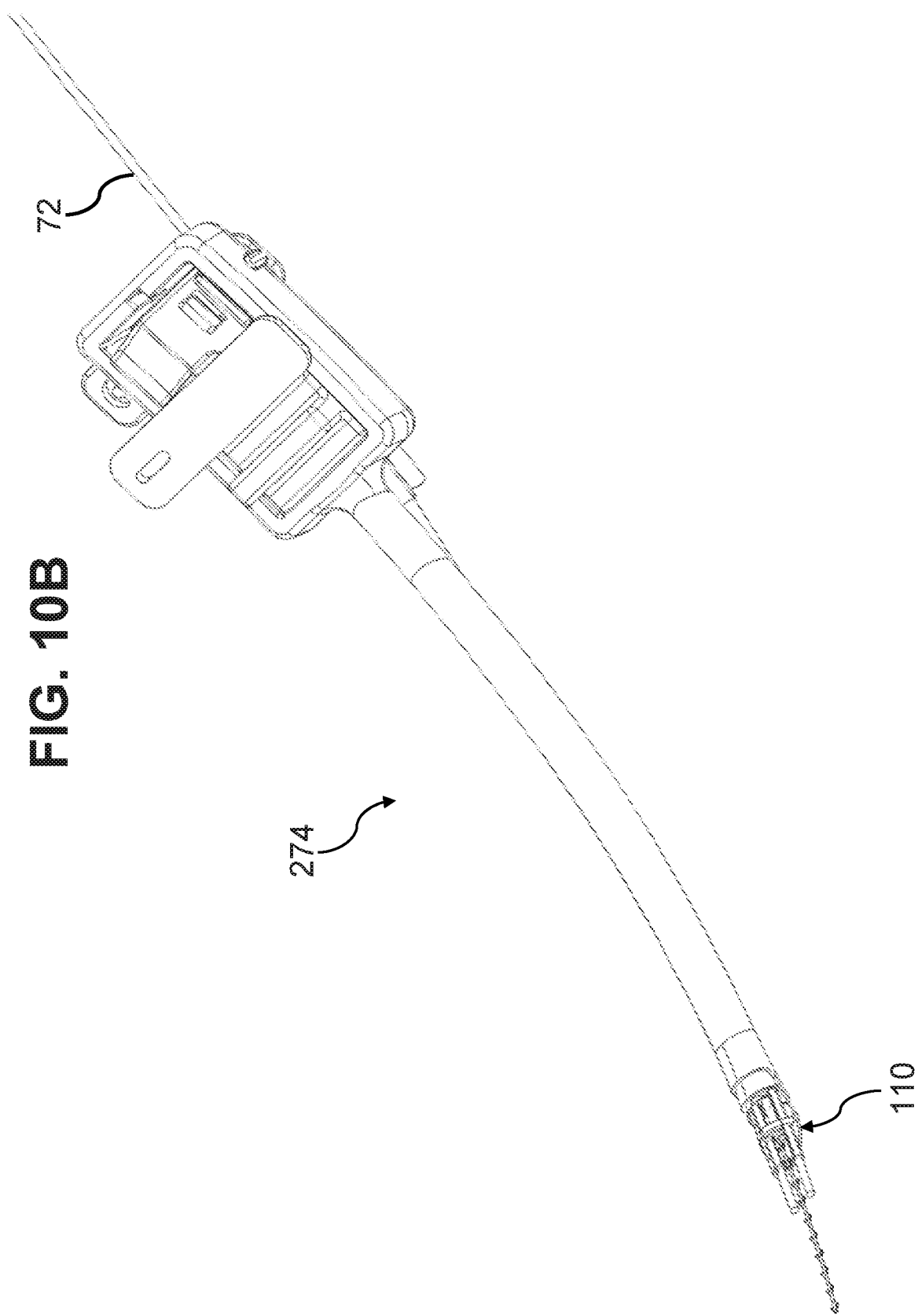
FIG. 10B is a perspective view of FIG. 10A.
Figure 10E:
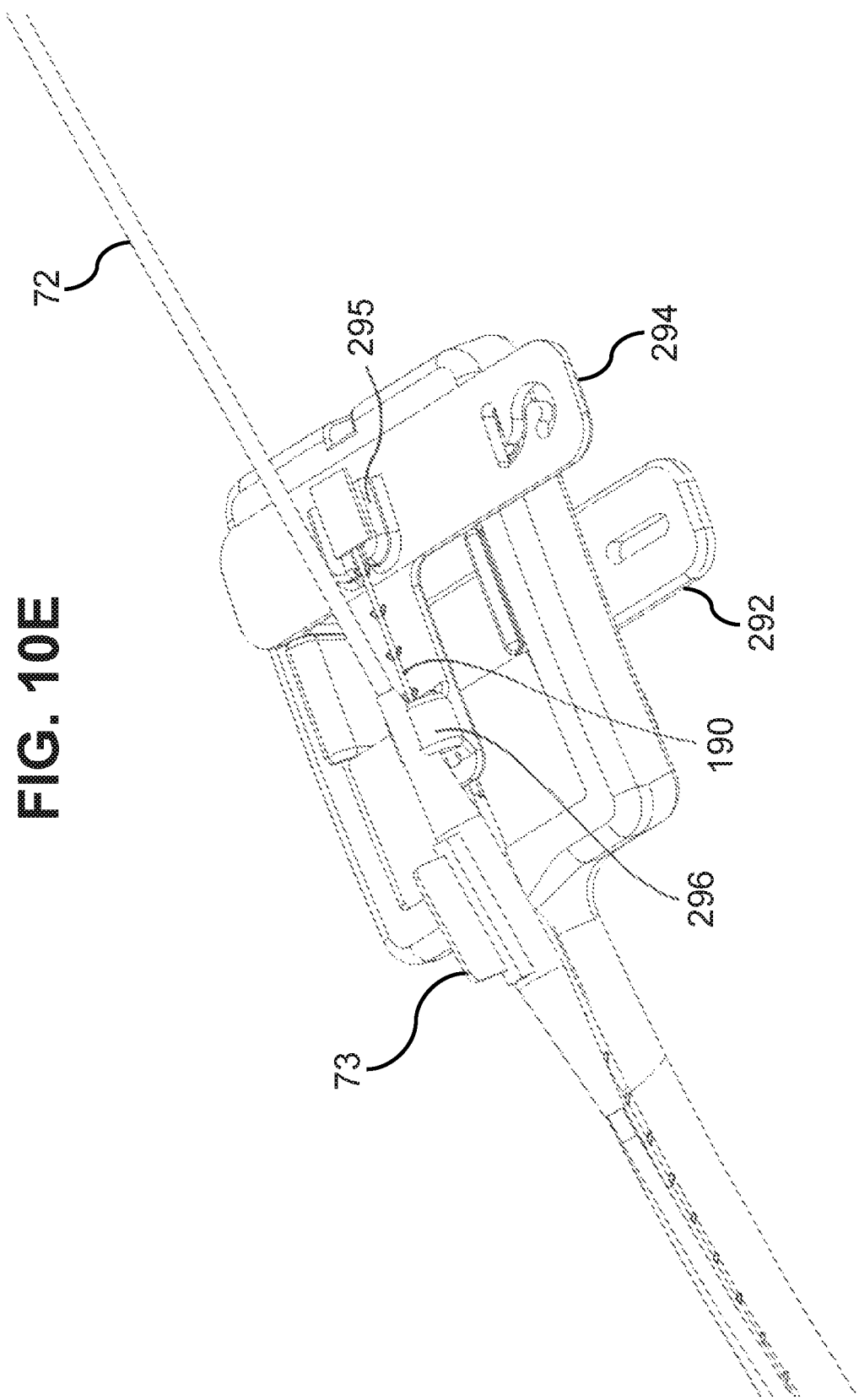
FIG. 10E is a closeup view of a second end of the electrode carrier portion of FIG. 10D.

Electrode structure 110 can also include an element 130 on the inactive side of electrode structure 110. Element 130 may take the form of a buckle, loop In an embodiment such as depicted in FIG. 10C, element 130 may comprise a raised or arched element extending generally across electrode structure 110. In an embodiment, element 130 may include a bar portion 132 raised above the inactive side of electrode structure 110 and secured to electrode structure 110 with struts on either end of a bar portion 132.

In an embodiment, electrode structure 110 further includes a mesh bundle 180 and a barbed suture 190. Mesh 180 may comprise a self-fixating mesh, similar to the type used in hernia repair, having many miniature gripping barbs configured to secure mesh 180 to surrounding bodily tissue. Mesh 180 may be secured to electrode structure 110 by way of element 130. Barbed suture 190 is of the conventional type, as known to persons skilled in the art, and may be secured to electrode structure 110 by way of element 130. In an embodiment, mesh 180 is sized and shaped similarly to backer 114. In embodiments, mesh 180 may be rolled, balled up, or otherwise bundled. In another embodiment, mesh 180 may be arranged to lie flat on backer 114.

Referring now to FIGS. 2-15, a system 200 is depicted for implanting electrode structure 110 and lead 72 in a minimally invasive procedure. Implant system 200 includes a guidewire delivery arrangement 202 and a lead delivery tool 204. Guidewire delivery arrangement 202 includes a guidewire delivery tool 226 and an introducer needle 240. Guidewire delivery tool 226 comprises a frame 228 having a channel or aperture 230 defined therein, and a receptacle 232. A shuttle 234 is configured to movably translate within channel 230, and a thumbscrew 236 is configured to selectively clamp a guidewire 210 to shuttle 234. Introducer needle 240 is of the conventional type, as known to persons skilled in the art, and includes a hub portion 242 and a needle portion 244. Hub portion 242 is configured to be releasably coupled to receptacle 232 of guidewire delivery tool 226.

Lead delivery tool 204 includes a dilator portion 252 releasably coupled to an electrode carrier portion 274. Dilator portion 252 includes a body 254, a first end 256, a second end 260 and a central lumen 268 extending through dilator portion 252. First end 256 can include a tapered tip 258. Second end 260 includes a shroud portion 262, an exposed portion 264, a suture recess 266 and a plurality of pin recesses 267. Dilator portion 252 further includes a hypotube 270 disposed within central lumen 268. In an embodiment, hypotube 270 extends to the end of tapered tip 258. In another embodiment, hypotube 270 does not fully extend to tip 258, thereby providing greater flexibility in tip 258.

Figure 17:
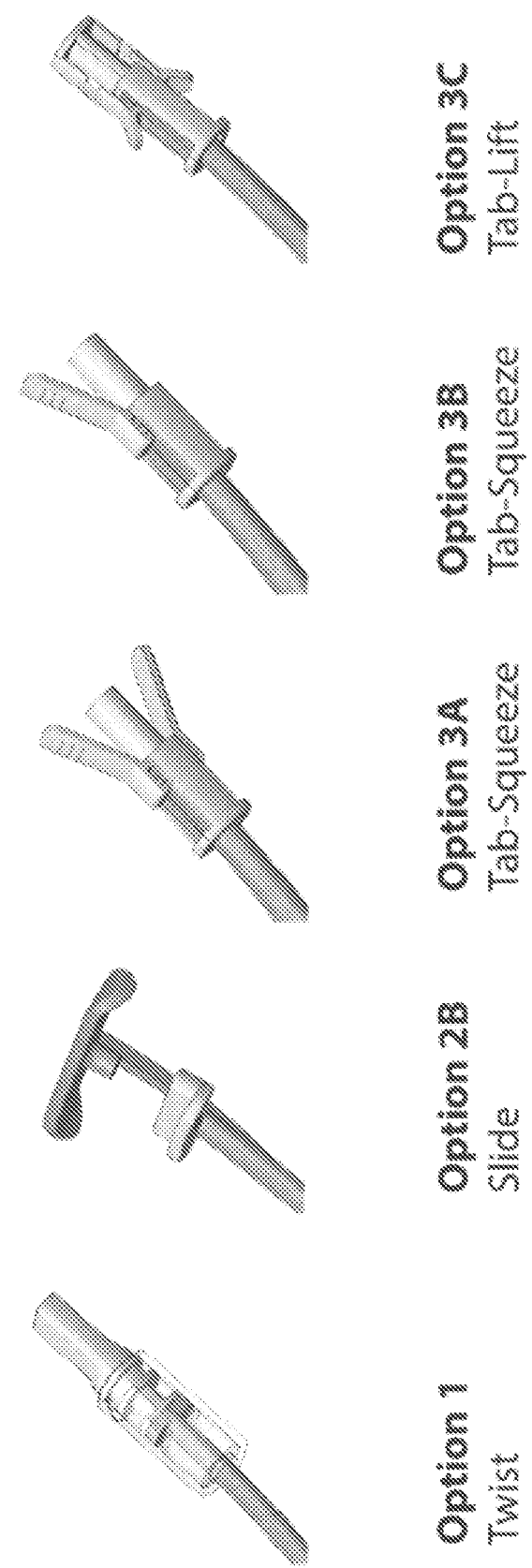
FIG. 17 is a perspective view of alternate release mechanisms, according to embodiments of the present disclosure.

Electrode carrier portion 274 of lead delivery tool 204 includes a body 276, a first end 280, a second end 282 and a central lumen 284 extending through electrode carrier portion 274. A channel 278 extends along the length of body 276. Electrode carrier portion 274 includes a release mechanism 286 comprising a slider 288 coupled to a plurality of pins 290. Release mechanism 286 can optionally include one or more safety release tabs, such as dilator release tab 292 and/or final release tab 294. Tab 294 may include a suture retention clip 295 and a lead retention clip 296. Alternate embodiments of release mechanism 286 are depicted in FIG. 17.

In an embodiment, hypotube 270 extends beyond second end 260 of dilator portion 252, with a length sufficient to extend beyond second end 282 of electrode carrier portion 274 when dilator portion 252 is coupled to electrode carrier portion 274. In another embodiment, each of dilator portion 252 and electrode carrier portion 274 include a hypotube having a length sufficient for the respective portions 252, 274.

As depicted generally in the Figures, lead delivery tool 204 is curved or arcuate along a length, and has a generally oval cross-sectional profile, such as depicted in FIG. 6.

Figure 2:
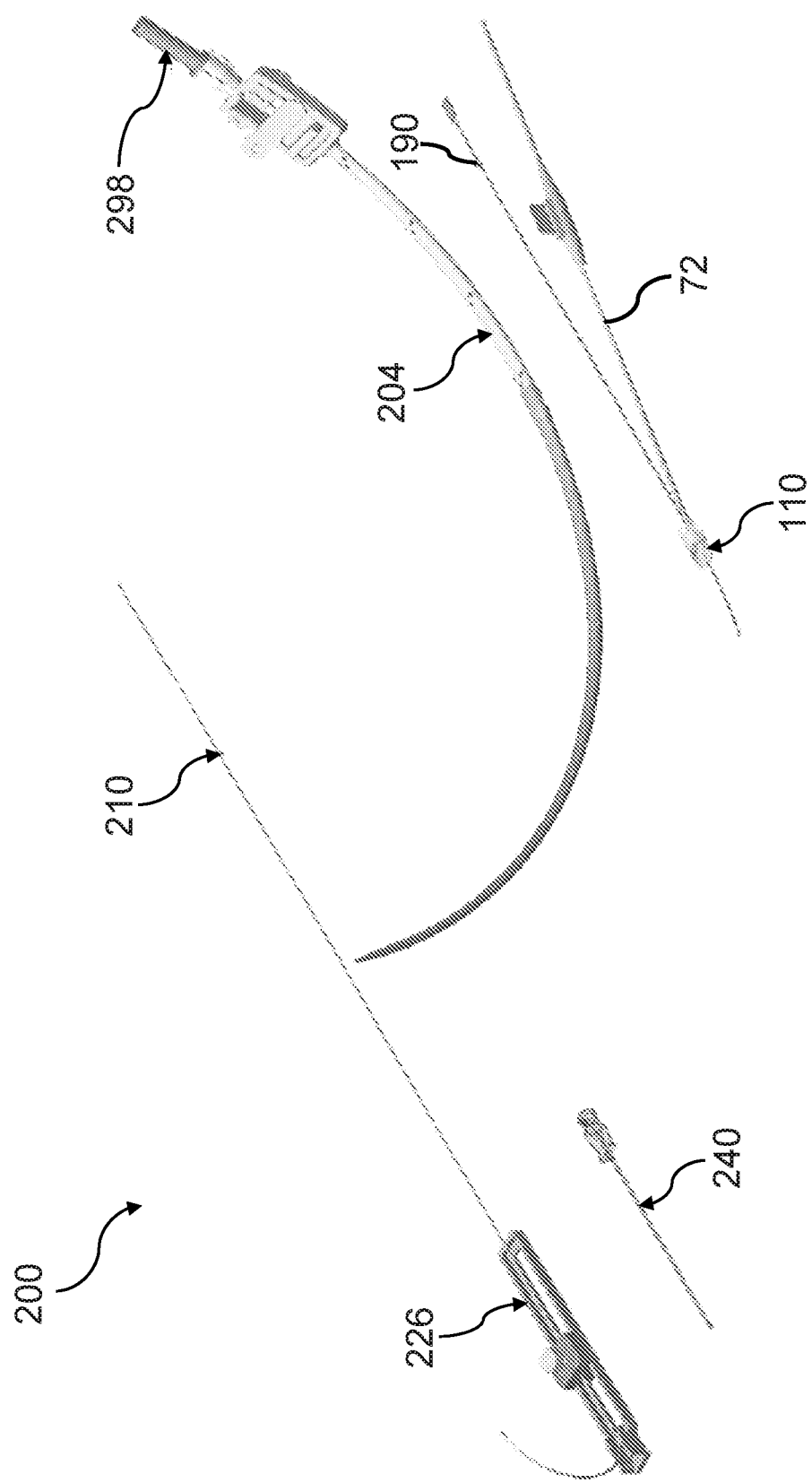
FIG. 2 is a perspective view of components of an implant system, according to embodiments of the present disclosure
Figure 3:
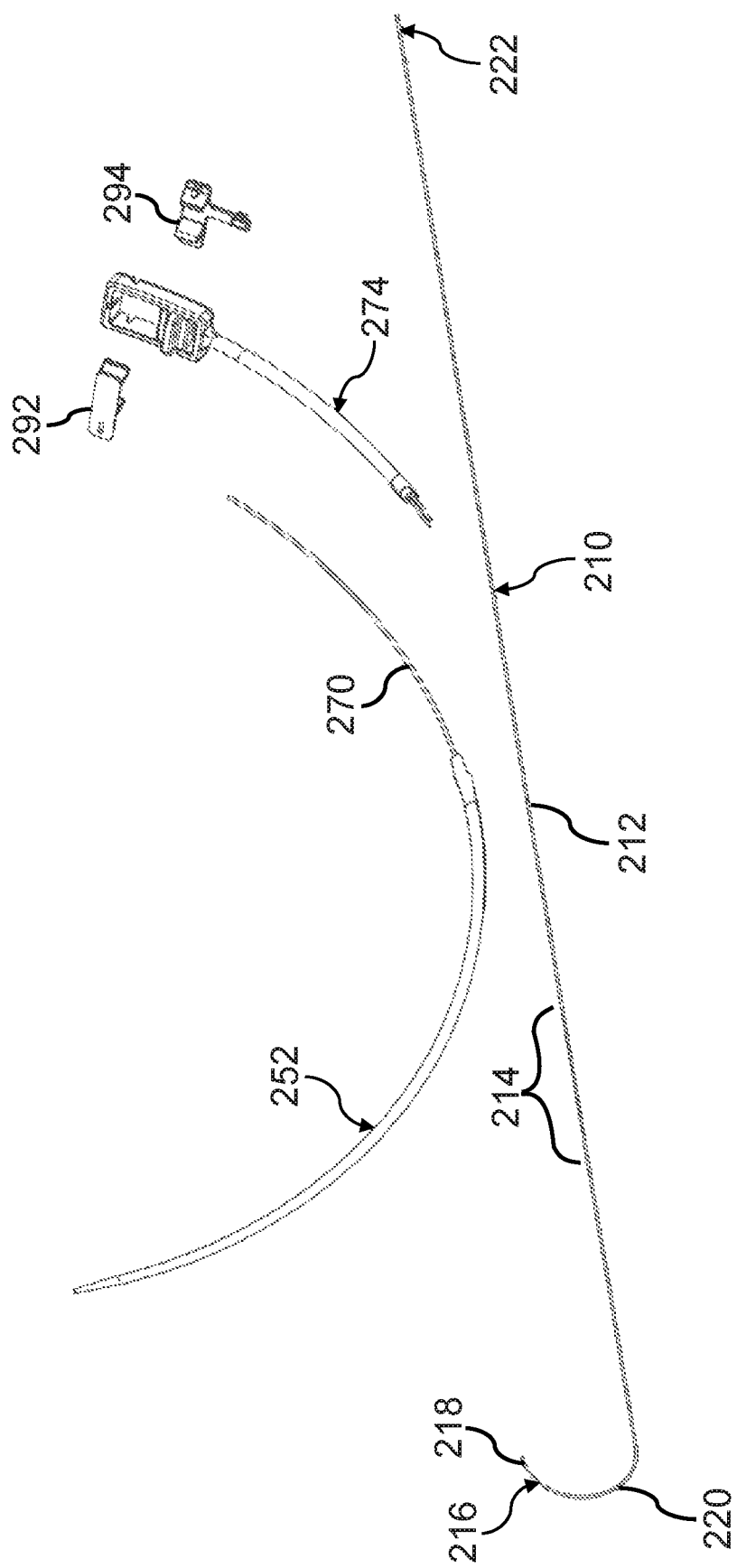
FIG. 3 is an exploded view of a dilator portion, an electrode carrier portion, and a guidewire of the system of FIG. 2.
Figure 4:
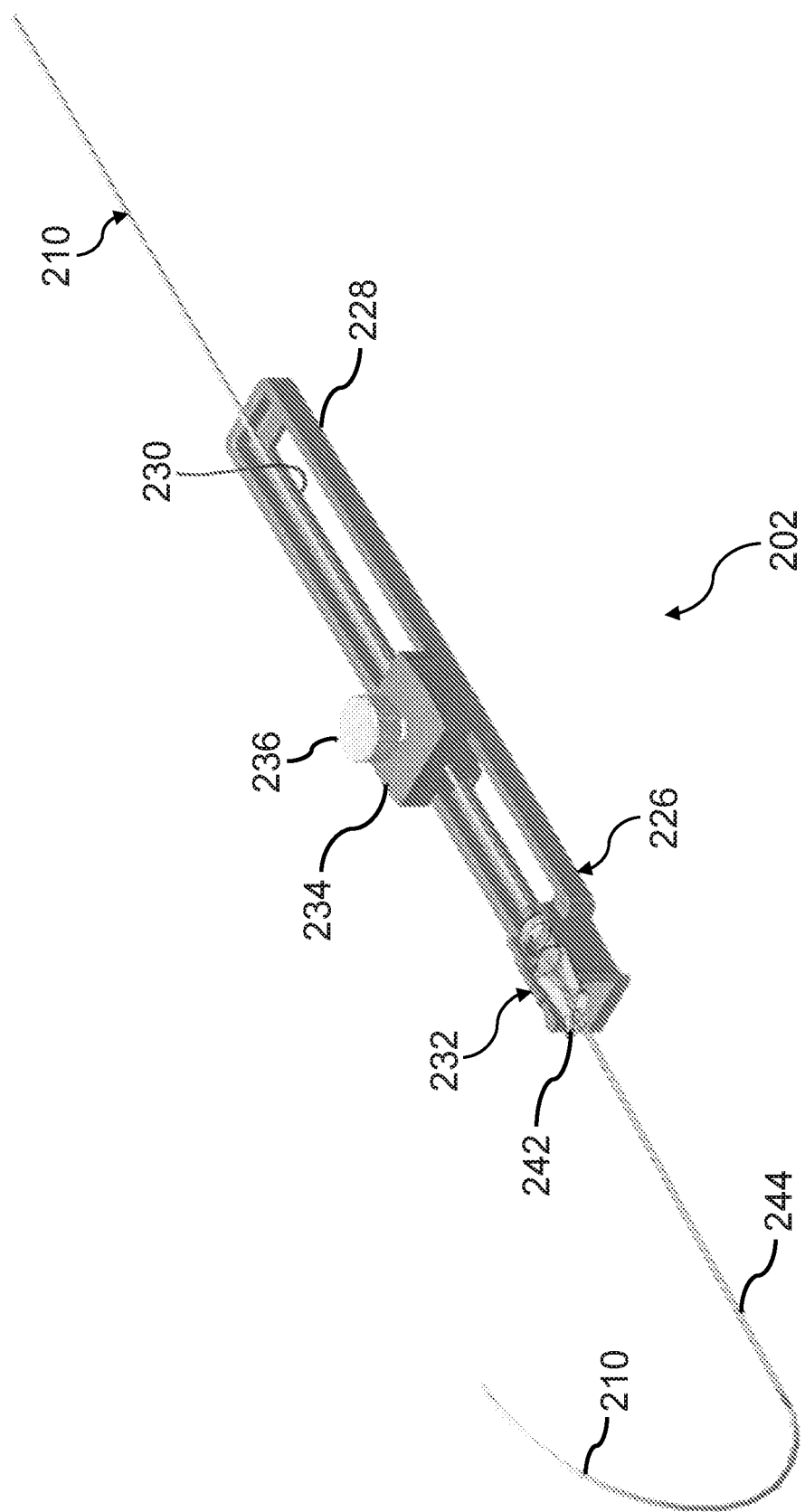
FIG. 4 is a perspective view of a guidewire delivery tool and guidewire of the system of FIG. 2.
Figure 5:
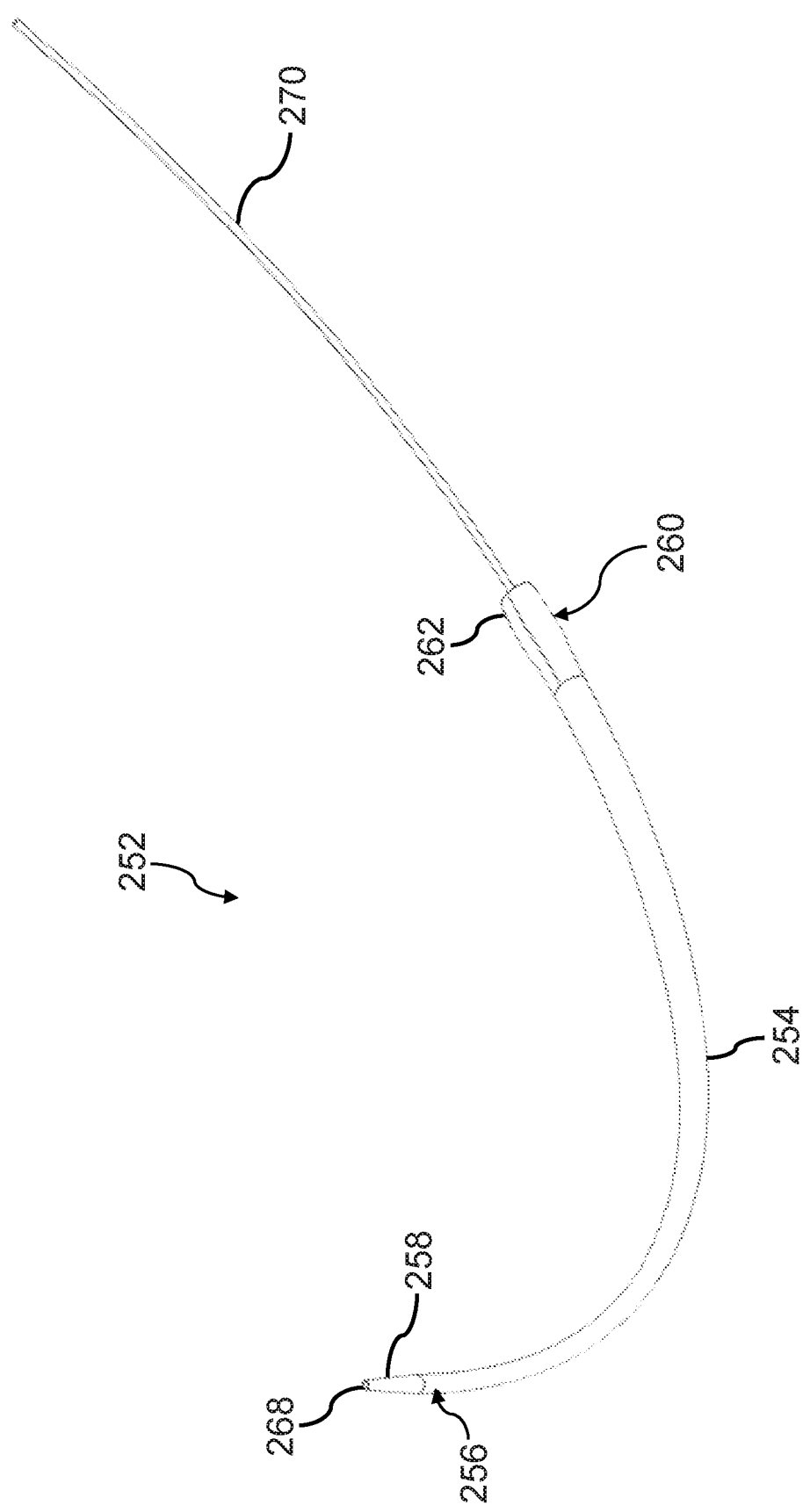
FIG. 5 is a perspective view of a dilator portion of the system of FIG. 2.

A conventional pin vise 298, as is known to persons skilled in the art, may be used to selectively clamp onto hypotube 270, thereby locking dilator portion 252 to electrode carrier portion 274 when assembled, as depicted in FIG. 2.

Guidewire 210 can be generally similar to conventional guidewires, but includes a number of improvements as part of system 200. Guidewire 210 includes a body 212, a first end 216 and a second end 222. First end 216 includes a tip 218 configured to facilitate piercing through body tissues. Tip 218 may include one or more bevels to increase sharpness and/or aid delivery through introducer needle 240. First end 216 of guidewire 210 can also include a pre-formed loop portion 220. In an embodiment wherein guidewire 210 is constructed of a shape-memory alloy such as nitinol, loop portion 220 is set as the default shape for first end 216 of guidewire 210. When introduced through needle 240, first end 216 of guidewire 210 will conform to the shape of needle 240.

The length and diameter of guidewire 210 may be selected as desired. In one embodiment, guidewire 210 has a diameter of approximately 0.035 inches and a length of approximately 32.0 inches. Further, the radius of curvature of loop portion 220 may be sized and selected as desired. In one embodiment, the radius of curvature of loop portion 220 may be approximately 0.5 inches. In another embodiment, the radius of curvature of loop portion 220 may be approximately 0.5 inches.

Generally the cross-sectional profile of body 212 can be circular, however, body 212 can include a flat surface 214 along at least a portion of a length of guidewire 210. Guidewire 210 may be oriented such that flat surface 214 provides a suitable surface against which thumbscrew 236 of guidewire delivery tool 226 can be tightened. Further, flat surface 214 may be arranged on guidewire 210 so as to provide an indication of orientation of loop portion 220 of guidewire 210 to the user. In an embodiment, flat surface 214 may be arranged on guidewire 210 such that in the default shape of guidewire 210, tip 218 at the end of loop portion 220 points toward flat surface 214.

Guidewire 210 may be supplied as part of system 200, or supplied separately. Similarly, pin vise 298 may be supplied as part of system 200, or supplied separately.

In operation, system 200 is used to implant electrode structure 110 and lead 72 in a patient in a minimally invasive procedure. In an embodiment, implant system 200 is used to implant electrode structure 110 and lead 72 on a carotid sinus of a patient.

Guidewire delivery arrangement 202 is prepared by securing introducer needle 240 to receptacle 232 of guidewire delivery tool 226. Guidewire 210 is passed through a lumen of shuttle 234 and into needle 244 such that first end 216 of guidewire 210 is within needle 244, causing loop portion 220 to straighten out. Guidewire 210 is rotated as needed to orient flat surface 214 under thumbscrew 236, and thumbscrew 236 is tightened down onto flat surface 214 to secure guidewire 214 therein.

Electrode structure 110 is prepared by securing mesh bundle 180 and barbed suture 190 thereto. On electrode carrier portion 274, slider 288 is moved to an advanced position such that pins 290 extend outwardly from first end 280 of electrode carrier portion 274. Electrode structure 110 is releasably coupled to electrode carrier portion 274 by passing pins 290 through element 130 of electrode structure 110. A portion of barbed suture 190 extending along the length of lead delivery tool 204 is arranged in channel 278 of electrode carrier portion 274, and lead body 72 is arranged over suture 190 in channel 278. Release tabs 292 and 294 are attached to release mechanism 286, preventing any unintended movement of slider 288. A portion of suture 190 is attached to clip 295 on release tab 294, and lead 72 is attached to clip 296 on release tab 284. FIGS. 10A-10E depict various views of electrode structure 110 and lead 72 loaded to electrode carrier portion 274.

Dilator portion 252 is then joined to electrode carrier portion 274, such that hypotube 270 extends through electrode carrier portion 274, pins 290 extend into pin recesses 267, and barbed suture 190 extends into suture recess 266 of dilator portion 252.

A conventional pin vise 298, as is known to persons skilled in the art, may be used to selectively clamp onto hypotube 270, thereby locking dilator portion 252 to electrode carrier portion 274. Lead delivery tool 204 is then fully assembled, as depicted in FIG. 11, and ready to be used in an implant procedure.

In an embodiment, system 200 is utilized to implant electrode structure 110 on or near a carotid sinus of a patient as described below. System 200 may also be used to implant electrode structure 110 at other anatomical locations using a similar approach.

The implant procedure generally includes guidewire delivery, lead delivery, electrode mapping, and electrode fixation. With a patient lying down, head turned, local anesthetic is administered to the patient. Ultrasound is utilized to locate the carotid sinus of the patient, and the skin of the patient may be marked accordingly. A small first incision is made caudally (inferior) of the location of the carotid sinus. Under ultrasound guidance, needle 244 of guidewire delivery arrangement 202 is inserted into the neck downward and toward the carotid sinus. With guidewire delivery arrangement 202 in a desired position, guidewire 210 may be advanced out of needle 244, such that first end 216 of guidewire 210 assumes the pre-formed loop shape 220. First end 216 of guidewire 210 will thus curve up towards the skin of the patient as guidewire 210 is advanced. If tip 218 of guidewire does not automatically exit through the skin, a second incision can be made. With guidewire 210 in position, guidewire delivery arrangement 202 can be removed.

Figure 12:
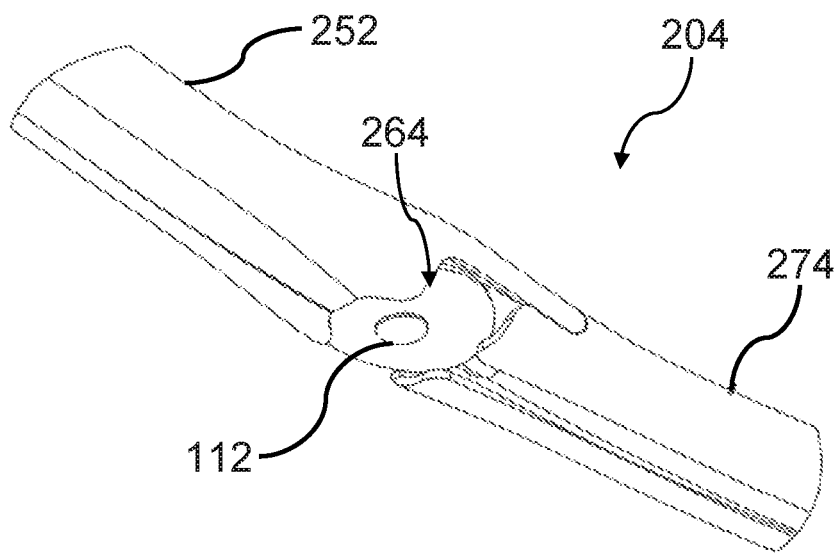
FIG. 12 is a closeup view of a portion of the lead delivery tool of FIG. 11, depicting the dilator portion coupled to the electrode carrier portion.

Lead delivery tool 204 can then be advanced over guidewire 210 by way of hypotube 270 until electrode structure 110 is proximate the carotid sinus. In the example procedure described herein, dilator portion 252 is oriented cranially while electrode carrier portion 274 is oriented caudally. A mapping procedure can then be performed to determine an optimal implant location for electrode structure 110. FIG. 12 depicts how electrode 112 is exposed through open bottom 264 of lead delivery tool 204. Lead 72 is attached to a stimulation source and electrical stimulation is delivered through electrode 112. One or more patient responses to the delivered stimulation are measured. Then lead delivery tool 204 is moved a small distance which in turn moves electrode structure 110 a small distance, and another stimulation delivered and response measured. The mapping procedure continues until a suitable implant location is found (with a corresponding satisfactory patient response to delivered stimulation). If the patient does not respond favorably to delivered stimulation despite mapping numerous locations, the procedure can be abandoned without implanting a baroreflex activation therapy system. Lead delivery tool 204 can be retracted caudally, guidewire 210 removed, and the incisions closed.

However, assuming the patient responds favorably to the delivered stimulation from at least one electrode position, the procedure continues. Guidewire 210 is removed from the patient, leaving lead delivery tool 204 in place. Pin vise 298 is removed, and dilator release tab 292 is removed, which allows slider 288 to be partially retracted. By retracting slider 288 to the point slider 288 hits final release tab 294, pins 290 are correspondingly retracted from recesses 267 in dilator portion 252, although pins 290 are not fully retracted and are still passing through element 130 of electrode structure 110.

Figure 13:
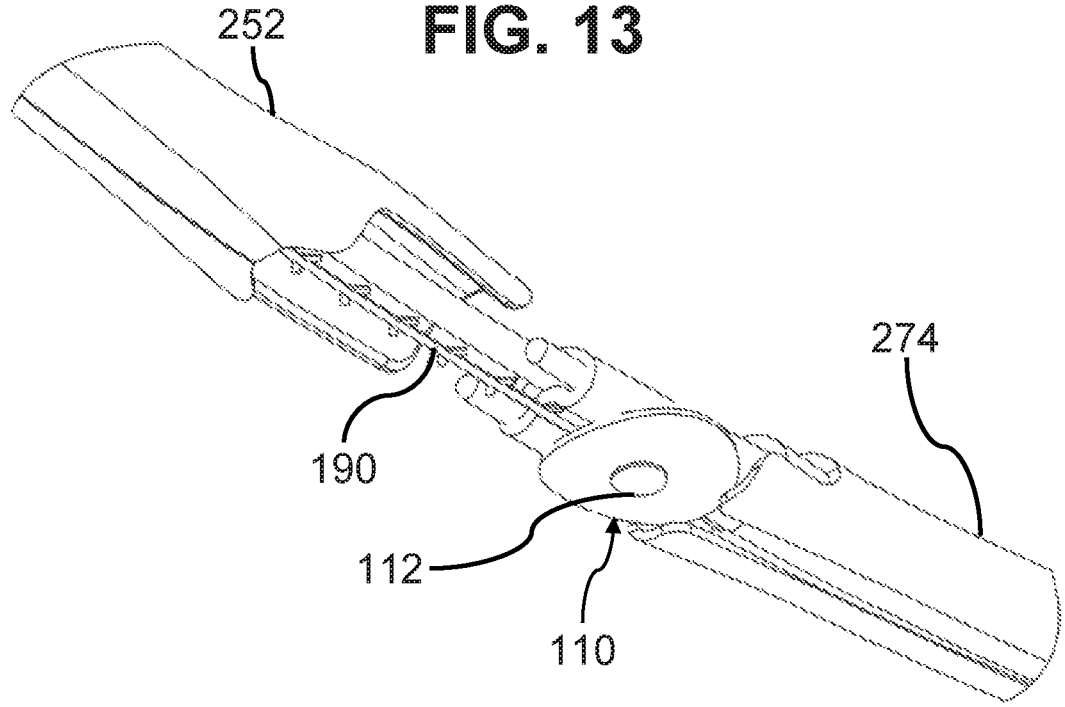
FIG. 13 is a closeup view of a portion of the lead delivery tool of FIG. 11, depicting the dilator portion partially separated from the electrode carrier portion.
Figure 14:
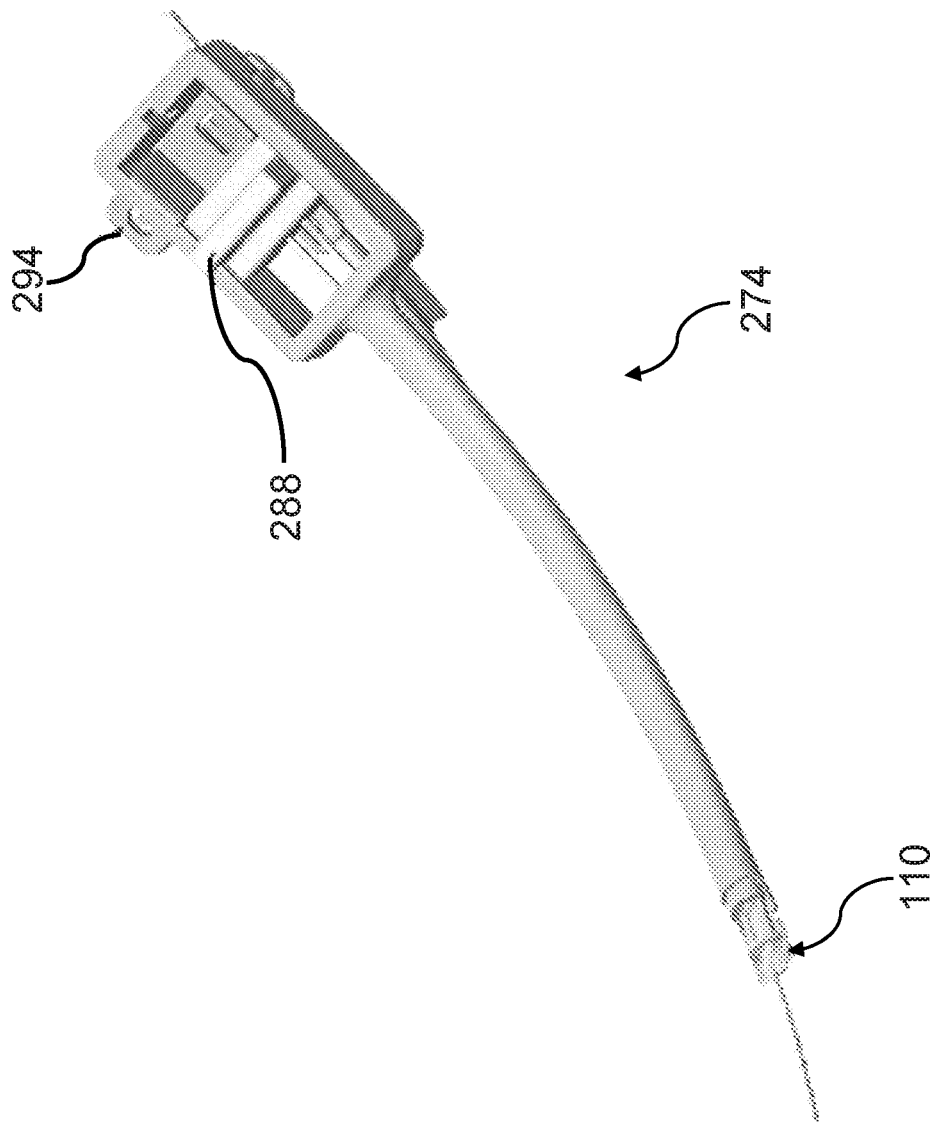
FIG. 14 is a perspective view of the electrode carrier portion of FIG. 10A, depicting a slider in a partially retracted position.

At this point, dilator portion 252 can be removed cranially from the patient. As dilator portion 252 is separated from electrode carrier portion 274, part of barbed suture 190 attached to electrode structure 110 begins to be exposed, and bundled mesh 180 may also be at least partially exposed, thereby helping maintain the position of electrode structure 110. FIG. 13 depicts dilator portion 252 partially separated from electrode carrier portion 274, and FIG. 14 depicts electrode carrier portion 274 alone, with electrode structure 110 exposed and slider 288 in a partially retracted position against release tab 294.

With dilator portion 252 removed, attention turns to electrode carrier portion 274. Lead 72 is detached from clip 296 of release tab 294, suture 190 is detached from clip 295 of release tab 294, and release tab 294 can then be removed. Slider 288 can then be fully retracted, causing pins 290 to correspondingly retract from element 130 of electrode structure 110. Electrode carrier portion 274 can then be removed caudally from the patient.

Figure 16:
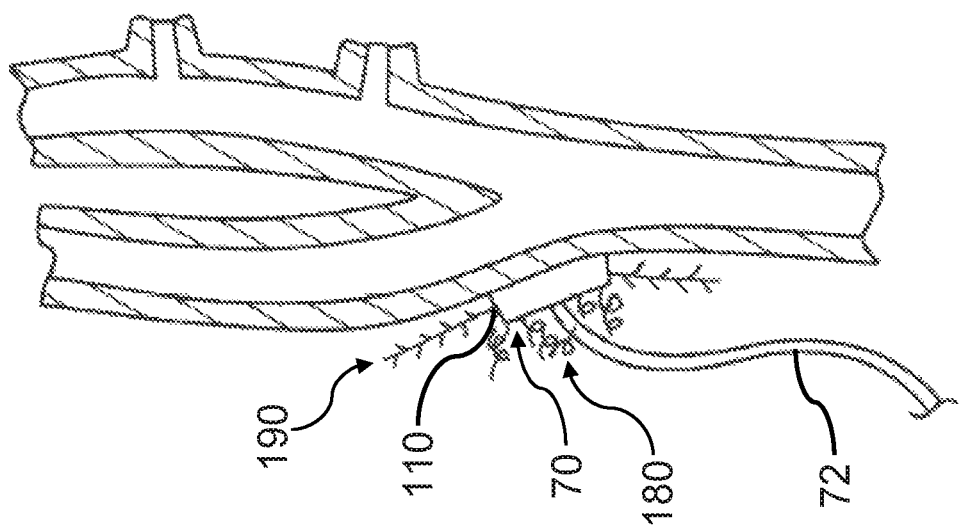
FIG. 16 is a closeup view of a portion of FIG. 15.
Figure 15:
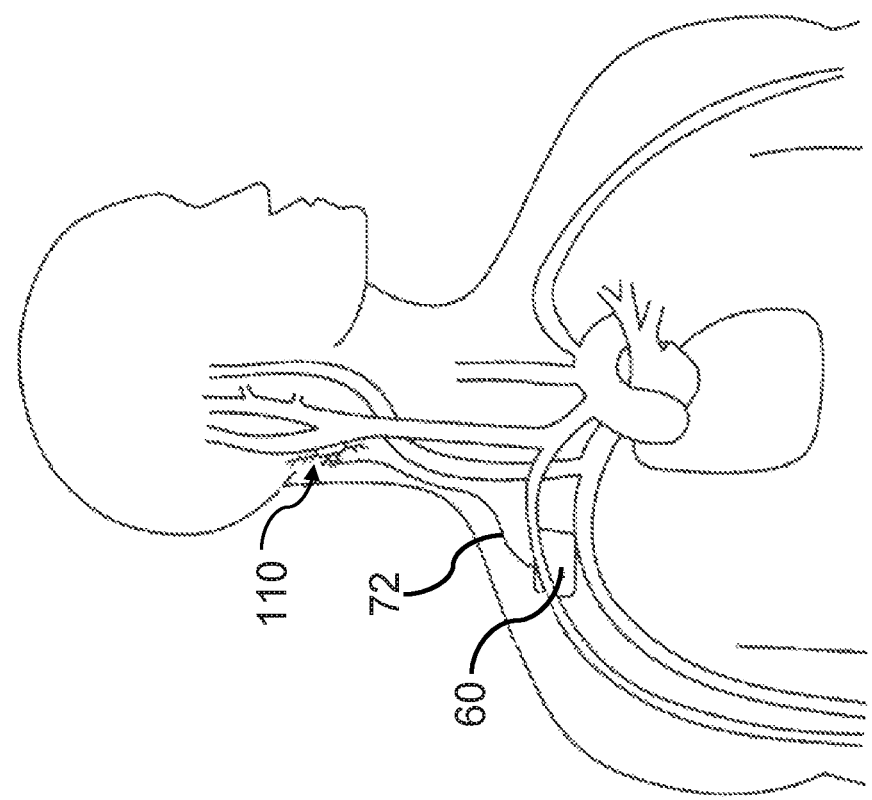
FIG. 15 is a schematic illustration of a baroreflex activation system implanted in a patient, according to embodiments of the present disclosure.

Any excess length of barbed suture 190 extending out of the incision can be trimmed as desired and tucked under the skin. A path may be tunneled for lead 72 from the electrode implant location to the implant location of control system 60 housing. If lead 72 includes a strain relief attachment tab 73, the tab can be sutured in place near electrode structure 110. The control system housing 60 is then implanted subcutaneously as known in the art, lead 72 is attached thereto, and the procedure is complete. FIGS. 15 and 16 are schematic representations of the implanted baroreflex activation therapy system.

When electrode structure 110 is implanted with system 200 as described herein, electrode structure 110 need not be sutured directly to the carotid sinus. Rather, barbed suture 190 maintains position of electrode structure 110 along a length of the carotid arteries, while bundled mesh 180 maintains position of electrode structure 110 in the direction between the skin and the carotid.

In an embodiment, a baroreflex therapy system can be provided to a user in a kit 400. Kit 400 may include a control system 60 in a housing, a baroreflex activation device 70 having at least one electrode structure 110 and coupled to the control system, implant system 200, and a set of instructions 410 recorded on a tangible medium for implanting, programming and/or operating the system. Kit 400 may be comprised of one or more hermetically sealed and sterilized packages. Instructions 410 may be provided as part of kit 400, or indications may be provided linking a user to electrically accessible instructions 410. Instructions 410 may include instructions for implanting electrode structure 110 and the baroreflex activation therapy system as described herein including the use of implant system 200 and/or a mapping procedure, and/or for programming and/or operating control system 60.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A device, comprising:
a dilator portion including a dilator body, a hypotube coupled to and extending from the dilator body, and a port disposed in the dilator body;
a carrier portion including a carrier body and a carrier lumen disposed therein; and
a release mechanism coupled to the carrier portion, the release mechanism including a movable pin and an actuator, the actuator operable to selectively advance and retract the pin with respect to the carrier body,
wherein the dilator portion and the carrier portion are selectively engagable, the hypotube of the dilator portion insertable into the carrier lumen, and further wherein the pin in an advanced position extends into the port of the dilator portion.

2. The device of claim 1, wherein the release mechanism further includes a first release tab, the first release tab configured to be coupleable to the carrier portion so as to prevent movement of the actuator and unintended separation of the dilator portion and the carrier portion.

3. The device of claim 2, wherein the release mechanism further includes a second release tab, the second release tab configured to be coupleable to the carrier portion so as to prevent movement of the actuator.

4. The device of claim 3, wherein the second release tab includes a retention clip configured for securing objects thereto.

5. The device of claim 1, wherein the carrier portion includes a channel extending along a length of the carrier body.

6. The device of claim 1, wherein the device includes an arcuate profile.

* * * * *